United States Patent [19]

Vernon et al.

[11] Patent Number: 5,278,498

[45] Date of Patent: Jan. 11, 1994

[54] SURFACE CONFORMING FLEXIBLE EDDY CURRENT PROBE FOR SCANNING VARYING SURFACE CONTOURS

[75] Inventors: Susan N. Vernon, Annandale, Va.; John M. Liu, Columbia, Md.

[73] Assignee: The United States of America as represented by the Secretary of the Navy, Washington, D.C.

[21] Appl. No.: 972,341

[22] Filed: Nov. 6, 1992

[51] Int. Cl.$^5$ .................... G01R 33/12; G01N 27/82
[52] U.S. Cl. .................................. 324/234; 324/262; 336/20
[58] Field of Search ............... 324/216, 234, 238, 236, 324/237, 239, 240, 262; 336/20

[56] References Cited

U.S. PATENT DOCUMENTS

| | | | |
|---|---|---|---|
| 3,862,247 | 1/1975 | Weltman et al. | 324/216 |
| 4,719,422 | 1/1988 | de Walle et al. | 324/238 |
| 4,922,201 | 5/1990 | Vernon et al. | 324/236 |
| 4,924,182 | 5/1990 | Vernon et al. | 324/237 |
| 4,965,517 | 10/1990 | Shelton et al. | 324/174 |

*Primary Examiner*—Walter E. Snow
*Attorney, Agent, or Firm*—John D. Lewis

[57] ABSTRACT

A flexible core eddy current probe is disclosed for testing of curved or irregular surfaces. The core is comprised of a flexible binder loaded with a powdered magnetic material and then formed into a specific flexible core shape continuously adaptable to irregular or curved surfaces. The flexible core probe has specific application to carbon fiber reinforced composite components having contoured surfaces.

16 Claims, 4 Drawing Sheets

SURFACE CONFORMING FLEXIBLE EDDY CURRENT PROBE FOR SCANNING VARYING SURFACE CONTOURS

The invention described herein may be manufactured and used by or for the Government of the United States of America for governmental purposes without the payment of any royalties thereon or therefor.

FIELD OF THE INVENTION

This invention relates to an electromagnetic test device for characterizing materials in terms of electromagnetic properties and localized anomalies. More specifically, the invention relates to eddy current probe core that serves to focus the electromagnetic field and is flexible to allow scanning of curved or irregular surfaces.

BACKGROUND OF THE INVENTION

Historically eddy current methods have been used to detect surface, or near surface, anomalies. When applied to carbon fiber reinforced composite materials, eddy current methods can be used to detect and measure a wide variety of anomalies, including the broken fibers associated with impact damage, misaligned fibers, and incomplete densification in carbon/carbon materials. Because many composite materials have high resistivities, inspection is not limited to the surface.

The depth to which a material can be inspected effectively depends on the dimensions of the anomaly to be detected. The diameter of the probe must be at least twice the depth to which the material is to be inspected, and ideally should be 4.5 times the depth. Sensitivity to small anomalies is inversely proportional to the size of the probe. Since significant anomalous regions in composites tend to be much larger than the small pits and cracks of interest in the inspection of metals, this larger size generally is not a drawback with respect to defect sensitivity.

In the past, ferrite cup core eddy current probes used to measure resistivity have been effective in inspecting carbon fiber reinforced composites such as is taught by U.S. Pat. Nos. 4,924,182 and 4,922,201 issued to Vernon et al. on 8 May 1990 and 1 May 1990 respectively. These ferrite cup cores are effective on planar surfaces.

Size is a factor when the composite material to be inspected has a curved surface. Eddy current probes should conform to the surface of the test material. When the thickness of the material to be inspected is large relative to the radius of curvature of the test material, the large probe that is required, if flat, will not conform to the surface. Commercially available axisymmetric cores can be ground to fit an inside diameter surface; grinding to fit an outside diameter surface is next to impossible. Elongated probes, fabricated by gluing together C-shaped or E-shaped cores, can be more easily made to conform to both outside diameter and inside diameter surfaces.

U.S. Pat. No. 4,719,422 issued to deWalle et al on Jan. 12, 1988 teaches a single purpose eddy current probe that is fabricated on a backing of flexible material, shaped to fit an irregular surface, and then made rigid. This results in a single purpose device which can be used to test a particularly shaped test material. When the radius of curvature varies over the surface to be scanned, such as in a rocket nozzle, a rigid probe cannot be used.

An important characteristic of braided carbon/carbon tubes is the exact alignment of carbon fiber toes. Eddy current methods could be useful if resistivity were measured as an elongated probe was rotated from the 0° direction (long axis of probe parallel to tube axis) to the 90° direction (long axis of probe parallel to circumferential direction). Resistivity values would be expected to correlate with fiber alignment between the 0° and 90° directions. The requirement that all parts of the active surface of the probe be equidistant from the surface of the test material, prevents the use of a single rigid elongated probe; when rotated from the 0° to the 90° position increasingly more of the probe surface would not be in contact with the tube. A set of probes would be required, each probe conforming to the surface at the particular orientation.

Adjustable radius probes have potential application to the inspection of components varying in both thickness and resistivity (aircraft wing skins, for example). This type of probe would allow both the separation of these effects and the inspection of a range of thicknesses using the optimum probe size without the need to physically change probes. Adjustable radius probes are made up of concentric ferrite rims and are difficult to fabricate using commercially available ferrite cores. The techniques of constructing an adjustable radius probe are disclosed in U.S. Pat. No. 5,021,738, issued to Vernon et al. on Jun. 4, 1991.

Conventional rigid core eddy current probes either are ineffecate in inspecting curved or irregular surfaces or must be specially fabricated to conform to the irregular surface and are thus limited to the particular shape of the test material and quite expensive as a single application item.

SUMMARY OF THE INVENTION

This invention teaches an eddy current probe that is flexible and its active surface can be conformed in shape to the surface of the test material. This flexibility makes the invention particularly effective in the testing of irregularly shaped or curved carbon fiber reinforced composites. The core may be formed of a polymer or other flexible material which is loaded with a powdered magnetic material.

Eddy current probes fabricated with cores made of ferrite-loaded silicone rubber RTV or other flexible binding material are flexible; they can be used to scan components with contours of varying radii. A typical application would be the inspection of rocket nozzles; the radius of curvature changes between the throat and the base, with additional curvature in the axial direction. Flexible binding material can be shaped into cores of any size and configuration, thus eliminating reliance on commercially available cores, designed for other purposes.

Cores of any size or configuration can be made by pressing the loaded binding material into a mold and allowed to cure. Alternatively, flat sections can be cured; the appropriate shapes cut out, and the pieces glued together with binding material. The flexibility of the probes permits the inspection of convex and concave surfaces with axisymmetric probes and the scanning of surfaces of varying curvature with both elongated and axisymmetric probes.

Therefore, it is an object of this invention to teach an eddy current core probe that is effective in testing curved or irregular surfaces.

It is a further object of the invention to teach an eddy current probe core that is flexible and may be manipulated to conform to the surface of the test material.

In a more complete understanding of the present invention and for further objects and advantages thereof, references may be made to the following description taken in conjunction with the accompanying drawings in which:

DETAILED DESCRIPTION OF THE PREFERRED EMBODIMENTS

The binding material in the prototype probes was a silicone rubber compound, General Electric RTV700 with 10% Beta-1 silicone curing agent. The manufacturer is the General Electric Company, Silicone Products Division, Waterford, N.Y. 12188. Other elastomeric polymers could also be used. If the issue is not flexibility but rather the fabrication of an inexpensive single-application ferrite core probe, the binding material could be a polymer that was rigid after cure.

Two types of fired 13 micron ferrite powders, type 33 and type 28, were recommended and provided by D. M. Steward Manufacturing Co., P.O. Box 510, Chattanooga, Tenn. 37401-0510. There are many other suppliers of ferrite and iron alloy materials which are suitable. The materials must have high resistivity. In initial tests the two types of powder tested had no discernable differences in their effects on probe characteristics and they were used interchangeably.

The ferrite powder was gradually mixed into the RTV700-Beta-1 mixture until the desired percent by weight of ferrite was achieved. 88% was the maximum amount of ferrite powder that could be mixed into the RTV binder without the latter losing its binding property. Since the purpose of the core is to provide maximum shielding and thus maximum focusing of the electromagnetic field with a flexible medium, 88% ferrite would be considered the best mode of practicing the invention. In instances where the probe is large (lowering the resonant frequency of the probe) and the high material resistivity requires a high inspection frequency, it might be useful to have less ferrite to lower the permeability of the core, thereby increasing the resonant frequency. The actual percentage of the ferrite powder/binding material depends upon the required size and operating frequency.

Cores of any size or configuration can be made by pressing the loaded binder into a mold and allowed to cure. Alternatively, flat pieces of the material can be cured; the appropriate shapes cut out, and the pieces glued together with binder. With RTV700-Beta-1 material used as the binder, curing takes place at room temperature.

Figure 1:
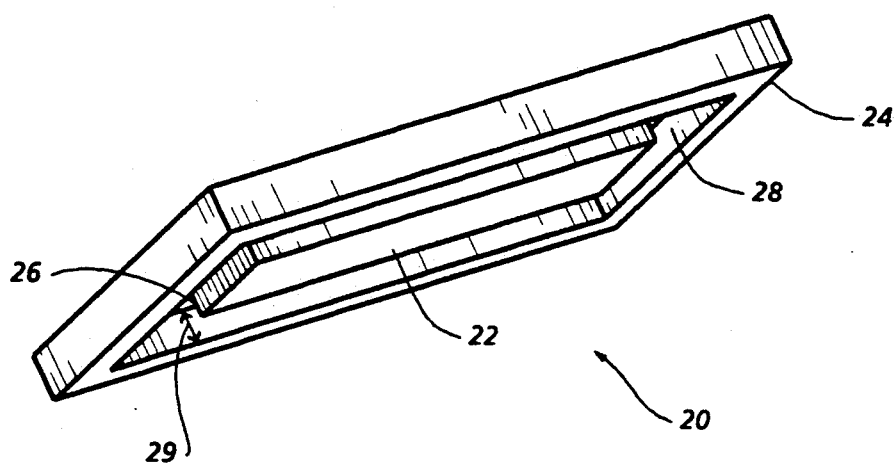
FIG. 1 is a perspective of a rectangular elongated cup core geometry of the present invention.
Figure 2:
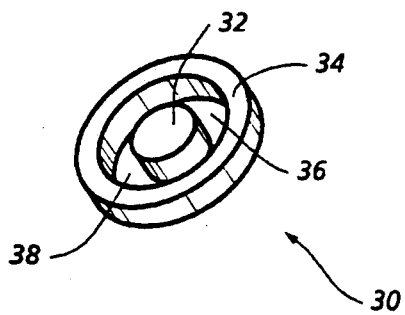
FIG. 2 is a perspective of an axisymmetric geometry of the flexible eddy current probe core of the present invention.

Among those probes tested were the elongated cup core probe of FIG. 1 and the axisymmetric cup core of FIG. 2. Turning now to FIG. 1, the elongated cup core embodiment 20 of the present invention is shown wherein a center post 22 is surrounded by a rectangular frame 24. Both center post 22 and frame 24 are held in place by a backing plate 26. All three of these elements are fabricated from the binding material and the ferrite powder discussed above. These three sections may be formed as a single unit in a mold without departing from the scope of the invention. Alternatively, these three sections, 22, 24 and 26 may be fabricated separately and affixed together with the binding material. The center post 22, rectangular frame 24 and backing plate 26 define a trough 28 with a depth 29 wherein a coil of wire will be disposed and held in place by a quantity of binding material mixed with an equal amount, by volume, of talc. The coil of wire should be ASW 33 or higher and will have leads exiting through access holes in the back plate 26 (holes not shown).

In the elongated probe core tested, the center post was 1.6 inches long and 0.2 inches wide with a depth of 0.075 inches. The frame 24 surrounding center post 22 was 2.5 inches long and 0.75 inches wide. Each side of the rectangle was 0.1 inches thick with the same depth as the center post 22 defining a trough depth of 0.075 inches surrounding center post 22. This results in a trough 28 having a width of 0.175 inches. The elongated cup core 20 of FIG. 1 is particularly applicable when directional properties of either an isotropic material or an anomalous region of a material are of interest.

The embodiment of FIG. 2 is an axisymmetric cup core 30 used when the anisotropic properties of the test material are not of interest. The embodiment of the axisymmetric core built and tested comprised a center post 32, an outer frame 34 and a backing plate 36 which defined a trough 38. The relative dimensions generally conform to those of conventional axisymmetric solid ferrite cup cores. The trough 38 will contain the coil of wire held in place with a mixture of binding material and talc as described above, but not shown in FIG. 2. Another embodiment can be fabricated by leaving the center post out of FIG. 2.

Figure 3:
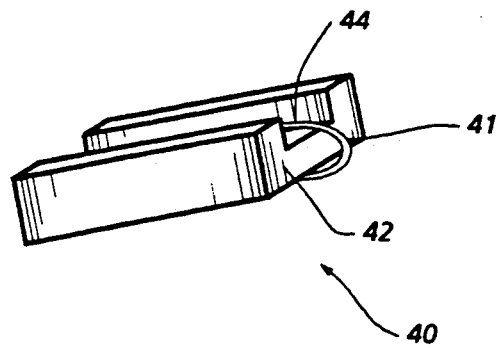
FIG. 3 is a perspective of the flexible eddy current probe core shaped in a "C" geometry.
Figure 4:
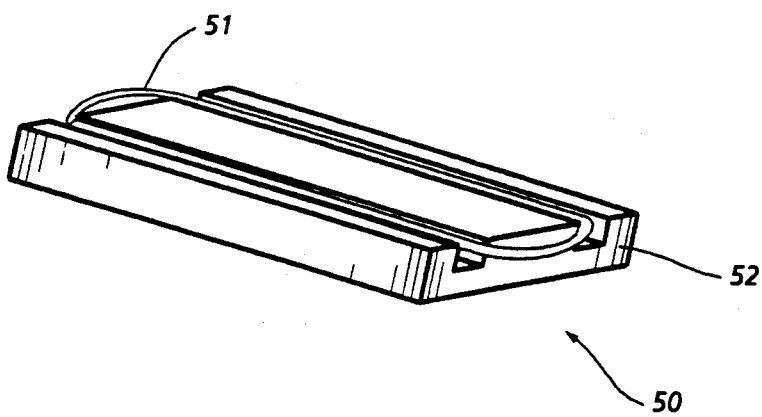
FIG. 4 is an eddy current probe using the flexible core of the present invention in the geometry of an "E" core.

FIG. 3 shows another embodiment of the present invention formed in the geometry of a rectangular "C" core 40. The embodiment of FIG. 3 is shown with a rectangular unipiece body 42 which defines the shape and trough 44. A coil of wire 41 is shown disposed in a conventional manner for a "C" cup core probe. Likewise, FIG. 4 depicts an "E" geometry cup core 50 formed of a unibody 52 wrapped with a coil 51 in a conventional manner.

Figure 5:
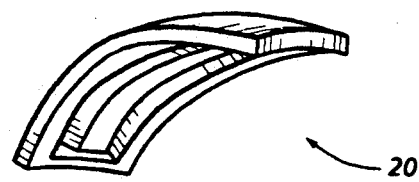
FIG. 5 is a perspective of one geometry of the eddy current core shown flexing to conform to a curved test surface.

FIG. 5 shows the elongated cup core 20 of FIG. 1 as it is flexed to conform to a test environment where it is necessary to conform the probe around a cylindrical test material with the probe oriented with its long axis at a 45 degree angle to the axis of the cylinder.

Figure 6:
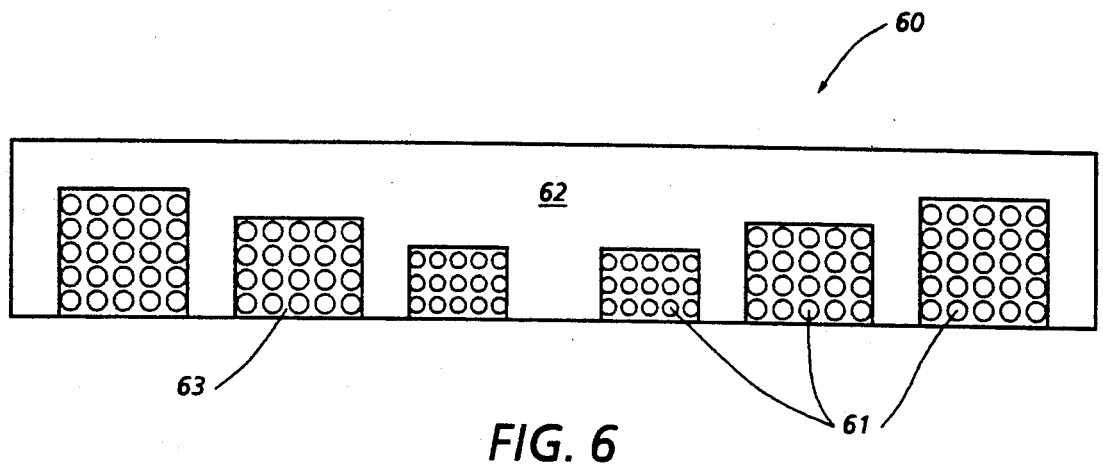
FIG. 6 is the present invention fabricated as an adjustable radius flexible eddy current probe.

FIG. 6 shows an adjustable radius eddy current coil probe 60 comprised of a variable radius cup core 62 containing multiple coils 61 held in place by a mixture of binding material and talc 63. The parameters and geometry of adjustable radius eddy current coil probes is taught in U.S. Pat. No. 5,021,738 by Vernon et al. issued Jun. 4, 1991. U.S. Pat. No. 5,021,738 is hereby incorporated by reference.

Figure 7:
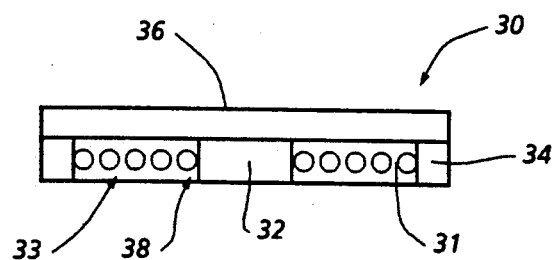
FIG. 7 is a cross-sectional view of the eddy current cup core of FIG. 2 showing the placement of a coil and the potting holding the coil in place.

FIG. 7 is a cross-sectional view of the axisymmetric embodiment of FIG. 2, item 30, showing a center post 32, an outer frame 34 and a backing plate 36. A coil of wire 31 is shown in trough 38 where it is potted in place with a mixture of talc and binding material 33.

The various embodiments illustrated by FIGS. 1-7 are by way of example and do not limit the scope of the invention. The number of turns of wire used in coils is determined by the inspection frequency and the impedance requirements of the impedance measurement device. The prototypes contained between 3 and 10 turns. The cup of the core containing the coil is filled with binding material mixed with an equal amount (by volume) of talc. The talc serves to stiffen the potting material so the bending of the coil conformed to the bending of the core. Wire sizes of ASW #33, or smaller, are required as larger wire was found to be stiffer than the core. Coil leads are brought out through small holes in the back plate section and soldered to a flexible lead attached to a BNC connector. A little binding material placed on the top of the back plate where the leads emerge provides some additional support to the leads.

Several tests were performed to measure the relative focusing capability and relative efficiency of the flexible core probes versus air-core and solid ferrite (100% ferrite) cores. The test materials were a titanium panel and a 2" outside diameter titanium cylinder. Data were collected at 7 frequencies from 12.5 kHz to 400 kHz. Measurements were made with a Hewlett Packard 4192A low frequency impedance analyzer.

Figure 8:
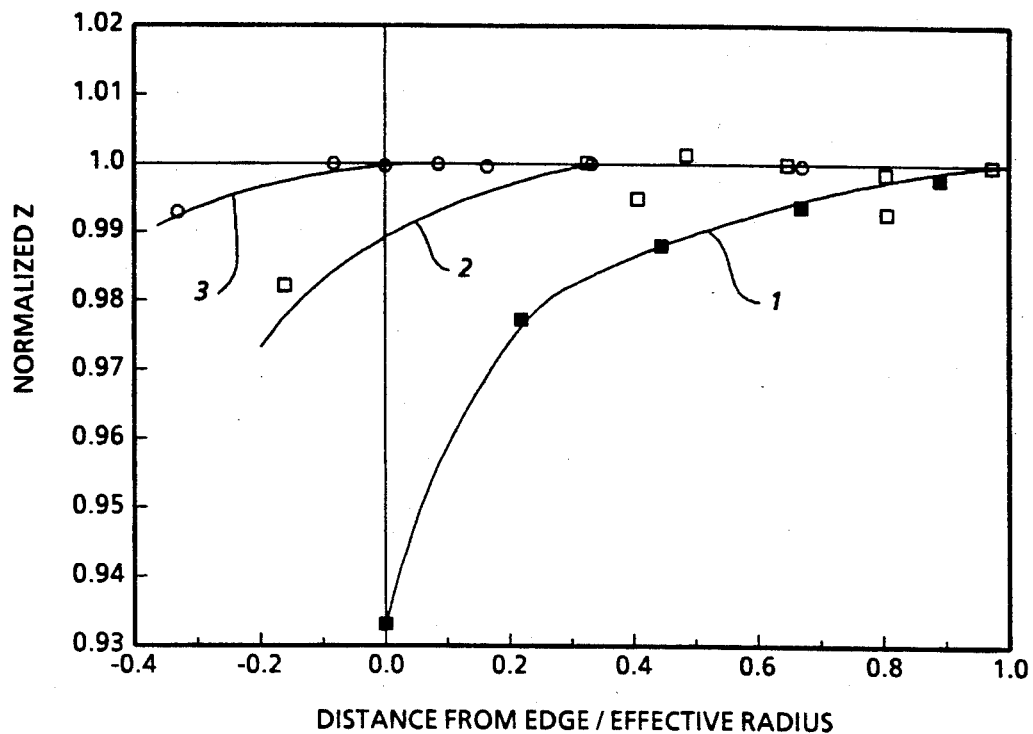
FIG. 8 is a graph of the normalized impedance versus the distance between the edge of a probe and the edge of a test material.

The relative focusing effects of the flexible core (88% ferrite), an air-core probe (no core), and a solid ferrite core were estimated in terms of the edge effect. The greater the shielding provided by the core, the more focused the field and the less the distance between the edge of the probe and the edge of the material before the field is disturbed by the edge of the material. The change in probe impedance, normalized with respect to the impedance of the probe far from the edge of the material, was measured as a function of the distance between the edge of the material and the edge of the probe normalized by the radius of the axisymmetric probe. In FIG. 8 normalized impedance is plotted against the distance between the edge of the probe and the edge of the material divided by the radius of the probe. It can be seen that the field of the air core probe illustrated by curve 1 seems to extend beyond the edge of the coil by a distance almost equal to the radius of the coil. In contrast, the field of the 88% ferrite core illustrated by curve 2 extends about a third of its radius, while the field of the 100% ferrite core, curve 3, does not extend beyond the edge of the probe.

Figure 9:
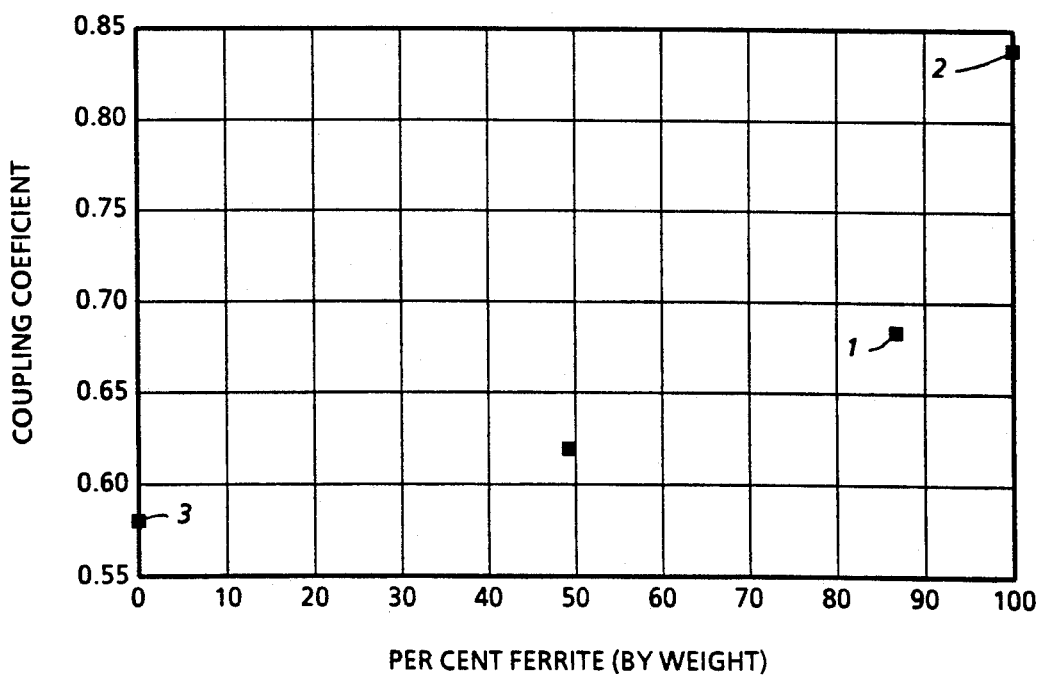
FIG. 9 is a plot of the coupling coefficient versus percent ferrite by weight.

The effect of the amount of ferrite powder in the cores on the efficiency with which the probe transmits energy to the test material was determined by measuring the coupling coefficient of a coil under four conditions. Two elongated cores, having 49% and 88% ferrite by weight were fabricated. A 10-turn coil to fit the trough was wound and set in unloaded binding material. The coupling coefficient was measured with the coil alone, in each of the flexible cores, and in a solid ferrite core of the same dimensions. The results, shown in FIG. 9, indicate that the 88% ferrite core, data point 1, is about 20% less efficient than the 100% ferrite core, data point 2, while the air core, data point 3, is about 30% less efficient.

Flexing or bending a probe would be expected to change the inductance of the probe since the relative positions of the turns of wire change during bending. Tests were performed to determine the extent of these effects and to determine if they could be compensated via normalization. The effects of flexing were determined under worse-case conditions. A 2.5-inch long probe was tested in conjunction with 2" diameter cylinders. A cycle consisted of a rotation of the probe from an initial 0° position with the long axis of the probe aligned along the long axis of the cylinder to a 90° position where the probe was wrapped around the cylinder, covering over a third of its circumference. The real and imaginary components of the impedance were measured every 10° from 0° to 90°. Data were collected alternately on a plexiglass cylinder and a titanium cylinder.

Figure 10:
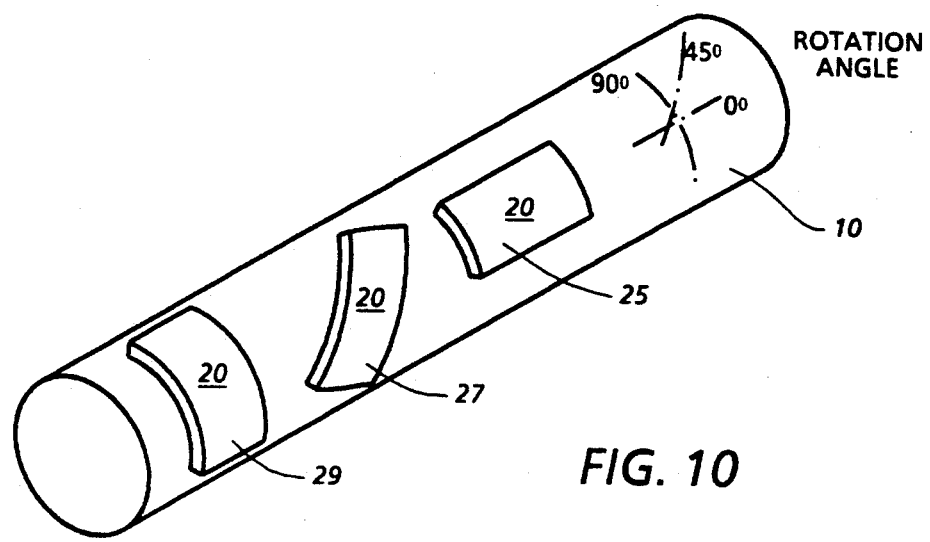
FIG. 10 is the present invention shown flexing around a test material.

FIG. 10 shows the flexing that occurs when an elongated probe 20 such as that illustrated in FIG. 1, is rotated on the surface of a cylinder 10. Therein, elongated probe 20 is shown with 0° between the long axis of probe 20 and axis of cylinder 10 illustrated at point 25 in FIG. 10. Point 27 shows the probe 20 rotated 45° and point 29 illustrates probe 20 rotated 90° to the axis of the cylinder. It is intuitive that probe 20 must flex and contort to remain flush with the surface of cylinder 10 throughout the rotation.

Figure 11:
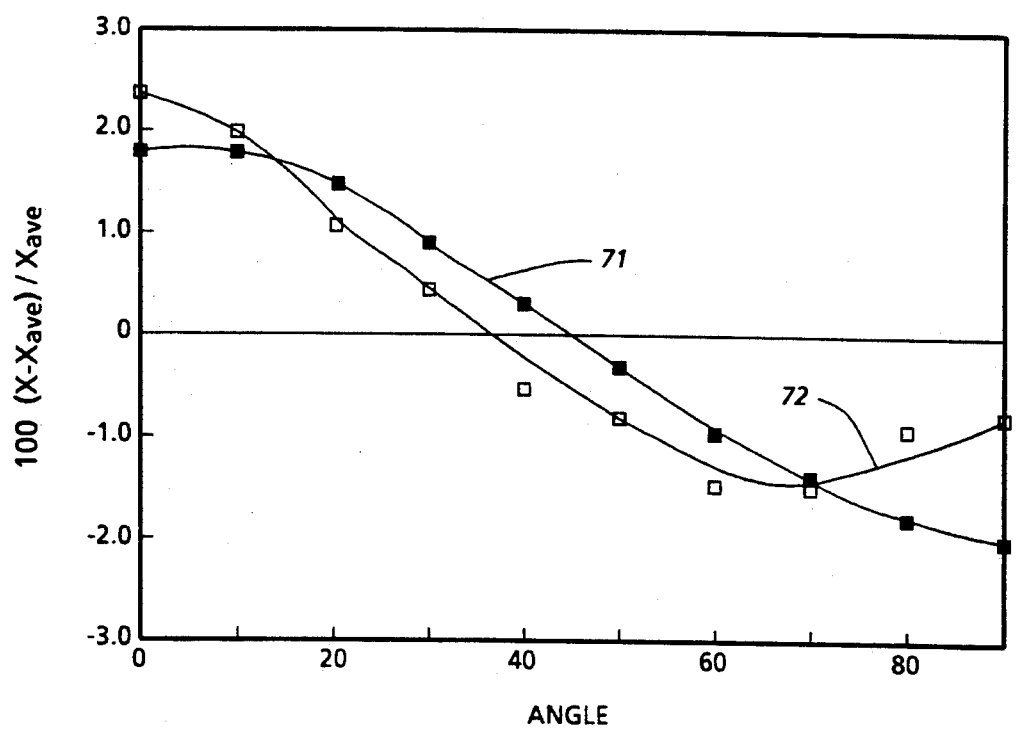
FIG. 11 is a graph showing the percent change in inductance versus test angle.

The effect of flexing the elongated probe from the 0° (aligned along the axis of the cylinder) to the 90° position (wrapped around the cylinder) on probe reactance is illustrated in FIG. 11. The percent change in normalized reactance both in air 71 and on titanium 72 is plotted against angle. This quantity varies from between approximately plus and minus 2% for both the air and titanium values. Scatter in titanium data is attributed to difficulties in maintaining constant pressure over the surface of the probe when it is in contact with the test material. The problem would probably be solved by the use of an effective mount rather than finger pressure as was the case for these data. To compensate for the inherent effects of bending the material, data can be normalized against data collected in air with the same degree of probe flexure. The real component varied less than 1% and the variation was random. There was no systematic change in reactance resulting from the number of times the probe was flexed. The change was less than 0.5 percent.

The flexibility of eddy current probes having ferrite-loaded binding material cores allows them to scan curved surfaces. The data must be normalized against air data collected as the probe is scanned over the surface of an identical nonconductive surface. These probes can be custom designed to any size and geometry. They should be used with a fixture that provides constant pressure over the surface of the probe.

Obviously, many modifications and variations of the present invention are possible in the light of the above teachings. It is therefore to be understood that within the scope of the appended claims the invention may be practiced otherwise than as specifically described.

What we claim is:

1. A surface conforming flexible core eddy current probe for inspection of curved or irregular surfaces comprising:
    a quantity of flexible binding material;
    a quantity of powdered magnetic material mixed in said flexible binding material whereby said quantity of powdered magnetic material comprises 49 to 99 percent by weight of the mixture of said binding material and said powdered magnetic material, forming a surface conforming eddy current probe core, and
    a coil of wire in close proximity to the mixture of said binding materials and said powdered material whereby an electromagnetic field is generated around said coil and focused by the mixture of said binding material and said powdered material forming the field of energy which is coupled to the curved or irregular surface to be inspected.

2. A flexible core eddy current probe according to claim 1 wherein said quantity of powdered magnetic material is a powdered ferrite.

3. A flexible core eddy current probe according to claim 1 wherein said quantity of powdered magnetic material is a powdered iron alloy.

4. A flexible core eddy current probe according to claim 1 wherein said binding material is an elastomeric polymer.

5. A flexible core eddy current probe according to claim 1 wherein said quantity of binding material is RTV 700 Silicone ® mixed with a Beta-1 curing agent.

6. A flexible core eddy current probe according to claim 1 wherein the mixture of said binder and said powdered material is formed as ring section connected to a backing plate section.

7. A flexible core eddy current probe according to claim 1 wherein the mixture of said binder and said powdered material is formed as a round center post section encircled by an outer ring section connected by a backing plate section to the center post.

8. A flexible core eddy current probe according to claim 1 wherein the mixture of said binder and said powdered material is formed as a rectangular center section surrounded by a rectangular frame connected by a packing plate.

9. A flexible core eddy current probe according to claim 1 wherein said binder and said powdered material is formed as an "E" shaped bar.

10. A flexible core eddy current probe according to claim 1 wherein said binder and said powdered material is formed into a "C" shaped bar.

11. A flexible core eddy current probe according to claim 1 wherein said binder and said powdered material is formed of a plurality of concentric ring sections defining a plurality of troughs surrounding a center post section and connected by a backing plate section and wherein said coil is formed of a plurality of individual sections which correspond to the troughs formed by the concentric ring sections of said binder and said powdered material and can be selectively activated.

12. A flexible core eddy current probe according to claim 11 wherein the troughs formed by said binder and said powdered material increase in depth as the diameter of the concentric ring sections which define the troughs increase in diameter.

13. A flexible core eddy current probe for inspection of curved or irregular surfaces comprising:
    a quantity of high resistivity elastomeric binding material;
    a quantity of powdered ferrite mixed in said high resistivity elastomeric binding material whereby said quantity of powdered ferrite comprises 88 percent by weight of the mixture forming a flexible eddy current probe core;
    a coil of wire in close proximity to the mixture whereby an electromagnetic field is generated around said coil and focused by the mixture forming an electromagnetic field which is coupled to the curved or irregular surface, and
    a quantity of potting material comprising an equal part by volume of talc and an elastomeric binding material to affix said coil in close proximity to the probe core formed by the mixture of said binding material and said powered ferrite.

14. A flexible core eddy current probe according to claim 13 wherein said quantity of powdered ferrite is a 13 micron, type 33 powder.

15. A flexible core eddy current probe according to claim 13 wherein said quantity of powdered ferrite is a 13 micron, type 28 powder.

16. A flexible core eddy current probe according to claim 1 further defined by a quantity of potting material comprising substantially equal parts by volume of talc and an elastomeric binding material to affix said coil of wire in close proximity to the probe core.

* * * * *